US007634316B2

(12) United States Patent
Swerdlow et al.

(10) Patent No.: US 7,634,316 B2
(45) Date of Patent: Dec. 15, 2009

(54) METHOD AND APPARATUS FOR VALIDATING A PACING TRAIN ASSOCIATED WITH T-SHOCK DELIVERY

(75) Inventors: Charles D. Swerdlow, Los Angeles, CA (US); William J. Havel, Maple Grove, MN (US)

(73) Assignees: Imperception, Inc., Los Angeles, CA (US); Medtronic, Inc., Minneapolis, MN (US)

( * ) Notice: Subject to any disclaimer, the term of this patent is extended or adjusted under 35 U.S.C. 154(b) by 459 days.

(21) Appl. No.: 11/117,593

(22) Filed: Apr. 28, 2005

(65) Prior Publication Data

US 2006/0247687 A1 Nov. 2, 2006

(51) Int. Cl.
*A61N 1/362* (2006.01)
(52) U.S. Cl. ......................................... 607/9
(58) Field of Classification Search .............. 607/8, 607/9, 4
See application file for complete search history.

(56) References Cited

U.S. PATENT DOCUMENTS

| 4,727,877 | A | 3/1988 | Kallok | 128/419 D |
|---|---|---|---|---|
| 5,117,824 | A | 6/1992 | Keimel et al. | 128/419 D |
| 5,129,392 | A | 7/1992 | Bardy et al. | 128/419 D |
| 5,163,427 | A | 11/1992 | Keimel | 128/419 D |
| 5,674,254 | A | 10/1997 | van Krieken | 607/11 |
| 5,741,312 | A | 4/1998 | Vonk et al. | 607/28 |
| 6,052,621 | A | 4/2000 | Begemann et al. | 607/28 |
| 6,393,316 | B1 | 5/2002 | Gillberg et al. | 600/515 |
| 6,647,292 | B1 | 11/2003 | Bardy et al. | 607/5 |
| 6,675,042 | B2 | 1/2004 | Swerdlow et al. | 607/8 |
| 6,954,672 | B1 * | 10/2005 | Parry et al. | 607/14 |
| 2004/0215248 | A1 | 10/2004 | Hess | |

FOREIGN PATENT DOCUMENTS

| EP | 0536873 A | 4/1993 |
|---|---|---|
| EP | 0922468 A | 6/1999 |
| WO | WO2004/026398 A | 4/2004 |

OTHER PUBLICATIONS

International Search Report, PCT/US2006/014761, Apr. 17, 2006, 7 Pages.

* cited by examiner

*Primary Examiner*—Carl H Layno
*Assistant Examiner*—Brian T Gedeon
(74) *Attorney, Agent, or Firm*—Michael C. Soldner (57) ABSTRACT

A method and apparatus for validating a cardiac pacing pulse train preceding a T-shock. Validation of the pacing pulse train includes verifying capture of at least the last pacing pulse of the pulse train and verifying that intrinsic ventricular events are not sensed during a pacing train interval that includes at least the interval between the last pacing pulse and a scheduled T-shock delivery. Capture verification may include sensing an event during an ER sensing window, morphological analysis of a sensed event, and analysis of the temporal relationship between sensed events occurring on different EGM sources. The scheduled T-shock is delivered in response to a valid pacing pulse train. A response to an invalid pacing pulse train may include any of an invalid pacing train notification, withholding a scheduled T-shock, extension of the pacing train, repeating the pacing train, or adjusting the pacing pulse train parameters.

22 Claims, 8 Drawing Sheets

METHOD AND APPARATUS FOR VALIDATING A PACING TRAIN ASSOCIATED WITH T-SHOCK DELIVERY

FIELD OF THE INVENTION

The present invention relates generally to cardiac electrophysiological testing in a medical device, and more particularly to a method and apparatus for validating a pacing train delivered prior to a T-shock such that the T-wave shock is delivered with a high probability of occurring during the vulnerable period.

BACKGROUND OF THE INVENTION

Delivery of a high-energy pulse during the vulnerable period of the cardiac cycle can induce ventricular fibrillation (VF) in patients. The vulnerable period encompasses the repolarization phase of the myocardial action potential, also referred to as the "recovery phase", and a period immediately following it. The repolarization phase is observed as the T-wave portion of a cardiac ECG or EGM. During the vulnerable period, the ventricles are in an inhomogeneous state where certain regions are excitable and certain regions are refractory to stimuli. Delivery of a stimulation pulse, or "T-shock", during this inhomogeneous state can initiate disorganized depolarization wave fronts causing fibrillation.

Patients undergoing implantation of an implantable cardioverter defibrillator (ICD) generally undergo electrophysiological testing to determine if the minimum shock energy required to terminate VF, referred to as the defibrillation threshold (DFT), meets the implant requirements for a particular ICD and lead configuration. In past practice, determination of the defibrillation threshold in a patient typically involved delivering a T-shock during the vulnerable period to induce VF and delivering a defibrillation shock there after to terminate the induced VF. A series of defibrillation shocks increasing or decreasing in energy can be delivered to determine the lowest energy that successfully defibrillates the heart.

A maximum T-shock energy exists, however, above which a T-shock pulse will not induce VF, even when delivered during the vulnerable period. The minimum T-shock energy at which VF induction does not occur is referred to as the "upper limit of vulnerability." The upper limit of vulnerability (ULV) has been shown to be a predictor of the defibrillation threshold in a patient. Determination of the ULV could be substituted for defibrillation threshold testing at the time of ICD implantation. Generally, the implanting physician only needs to know if the patient meets the ICD implant criteria, i.e. if the patient's defibrillation threshold is acceptably below the maximum defibrillation shock energy available from the ICD. A clinician may select a shock energy that would be an acceptable DFT for a particular ICD and lead configuration. If VF is not induced by a T-shock delivered at the selected shock energy, the energy is assumed to be at or above the ULV for that patient. The clinician can therefore conclude that the selected shock energy is at or above the patient's DFT and thereby make the determination that the patient meets the ICD implant criteria. Using ULV measurements, a determination that a patient meets ICD implant criteria may be made by delivering as few as one T-shock without actually inducing VF. Such methods potentially improve the safety of ICD implantation procedures since actual VF induction may be avoided.

A T-shock that is less than the ULV will normally induce VF in susceptible patients when it is properly timed during the vulnerable period. However, such a T-shock delivered outside the vulnerable period may not induce VF, potentially misleading a clinician to think the T-shock energy is greater than the ULV. In order to properly couple the T-shock to the vulnerable period, a T-shock is typically delivered following a train of pacing pulses delivered at a rate greater than the patient's intrinsic heart rate. The T-shock is delivered following the last pacing pulse at a coupling interval that corresponds to a previously measured time interval between a pacing pulse and a subsequent T-wave. If all of the pacing pulses in the pulse train capture the heart, the pace-T-wave interval will be consistent and a T-shock delivered at that interval following the last pacing pulse will fall into the vulnerable period.

However, if one or more pacing pulses do not capture the heart, or if an intrinsic event occurs prior to T-shock delivery, the timing of the vulnerable period may change relative to the last pacing pulse of the pacing train. The T-shock may fail to induce VF irrespective of its amplitude. Without recognizing that the ventricular response to the pacing train has changed, a clinician may inappropriately conclude that the T-shock energy is above the patient's ULV. Inappropriate ULV determination may cause a clinician to determine that a patient's DFT is lower than it actually is and that the patient meets ICD implant criteria when he/she may not. Methods are needed for promoting reliable T-shock delivery during the vulnerable period in order to take advantage of using ULV determination during ICD implantation procedures.

BRIEF SUMMARY OF THE INVENTION

The present invention provides a method and apparatus for validating a pacing pulse train, also referred to herein as an "S1 train", which precedes a T-shock. In order to promote accurate timing of a T-shock during the vulnerable period following the last pacing pulse of a preceding S1 train, at least the last pacing pulse must capture the heart and other intervening intrinsic events between the last S1 pulse and the T-shock should not be present. If one or more of the S1 pacing pulses fail to capture or if an intervening intrinsic event occurs during the S1 train, a previously set pace-T-shock interval may no longer be the correct coupling interval for timing the T-shock during the vulnerable period.

One aspect of the invention is a T-shock delivery method that includes validation of the S1 train. Validation of the S1 train includes verifying capture of at least the last pulse of the S1 train. Capture verification may be performed for all or any portion of the S1 pulses that includes the last S1 pulse. In one embodiment, capture verification includes detection of an evoked response (ER) during an ER sensing window. In another embodiment capture verification of an S1 pulse includes morphological analysis of a sensed event for verifying the sensed event is an ER. In yet another embodiment, capture verification of an S1 pulse includes analyzing the temporal relationship of sensed events occurring on multiple EGM signal sources for verifying the sensed events represent an ER.

Validation of the S1 train may further include sensing for intrinsic ventricular events during or after the S1 train, prior to T-shock delivery. In one embodiment, a sensed event that occurs outside an ER sensing window is determined to be an intrinsic event. In another embodiment, a sensed event that is not confirmed to be an ER based on morphological analysis or the temporal relationship of events on multiple EGM signals is determined to be an intrinsic event. An S1 train is declared valid if a capture requirement is met and intrinsic events that might alter the refractory period of the heart relative to the last S1 pacing pulse are not sensed.

Another aspect of the invention is a T-shock delivery method that includes a response to a detection of an invalid S1 train. Detection of an invalid S1 train may be based on failure of an S1 train to meet a previously defined capture requirement. Detection of an invalid S1 train may also be based on sensing of an intrinsic ventricular event during the S1 train, preceding a scheduled T-shock. In one embodiment, the response to an invalid S1 train includes the generation an alert signal to notify a user of the invalid S1 train. In another embodiment, the response to an invalid S1 train includes canceling a scheduled T-shock. In other embodiments, the invalid S1 train response includes automatically extending the duration of the S1 train or repeating delivery of the S1 train. In still other embodiments, the invalid S1 train response includes adjustment of the S1 pacing train parameters.

Another aspect of the invention is an apparatus capable of validating an S1 train. The apparatus includes control circuitry for controlling the delivery of an S1 pacing train generated by low-voltage output circuitry and for controlling the delivery of a subsequent T-shock pulse generated by high voltage output circuitry. The apparatus includes low-voltage cardiac pacing electrodes adapted for coupling to the low voltage output circuitry and high-voltage electrodes adapted for coupling to the high voltage output circuitry. The apparatus further includes sensing circuitry for receiving EGM or ECG signals from one or more sources using the low and/or high voltage electrodes for sensing ventricular events. Sensed signals are provided to processing circuitry for identifying a sensed event as an ER or as an intrinsic event.

Processing circuitry is used to validate an S1 pacing train based on an S1 capture requirement and criteria regarding the occurrence of sensed intrinsic events.

Another aspect of the invention is a computer-readable medium containing instructions. The instructions cause a programmable processor to control a defibrillator to deliver an S1 pacing train; validate the S1 pacing train by performing capture verification methods and sensing for intrinsic ventricular events during the S1 pacing train prior to T-shock delivery; deliver a T-shock at a predetermined pace-T-shock interval if an S1 pacing train is validated; and provide an invalid S1 pacing train response if an S1 pacing train is invalidated. A response to an invalid S1 pacing train may include any of: generating an alert; withholding a T-shock; extending the S1 pacing train; repeating the S1 pacing train, adjusting a pacing train parameter.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION

The present invention is directed toward providing an apparatus and method for validating an S1 pacing train preceding a T-shock. In past practice, T-shock delivery for inducing VF during DFT testing could be repeated until VF was successfully induced. The goal was to induce VF. If a T-shock failed to induce, the timing or the T-shock energy could be adjusted until VF induction was successful. The reason for a failed induction, whether it be mistiming of the T-shock or the T-shock energy level, was not important to the results of a DFT test. Since the goal of ULV measurements is to determine a T-shock energy that does not induce VF, timing of the T-shock during the vulnerable period is critical in determining an accurate ULV. Furthermore, electrophysiological testing of a patient's susceptibility to arrhythmias requires accurate timing of T-shocks during the vulnerable period.

In order to promote certainty that the T-shock occurs during the vulnerable period, at least the last pacing pulse in the S1 pacing train preceding the T-shock must capture the ventricles without the occurrence of intervening intrinsic events. Loss of capture during the S1 train or intervening intrinsic ventricular events could alter the vulnerable period timing relative to the last S1 pacing pulse. As such, the present invention provides a method and apparatus for verifying capture and detecting intrinsic ventricular events during an S1 pacing train and prior to T-shock delivery. The present invention may be implemented in an ICD system, for example, for use during DFT testing or ULV measurements used to determine if a patient meets ICD implant requirements.

The invention may alternatively be implemented in an automatic external defibrillator (AED). AEDs are increasingly provided for use in public and private environments. The S1 pacing train validation methods described herein may be implemented in an AED having T-shock delivery features that may be used for inducing VF, measuring DFT or measuring ULV.

Figure 1:
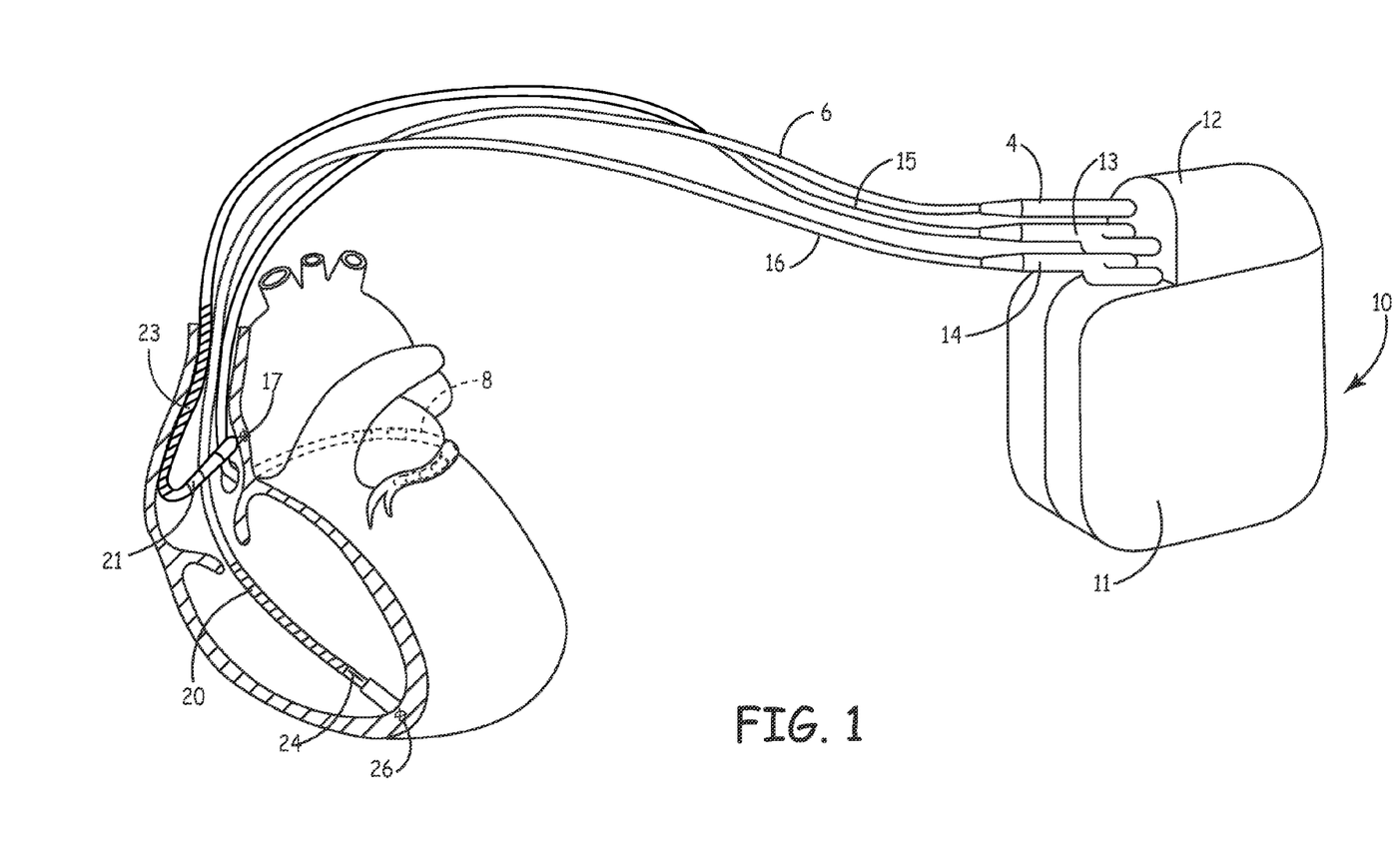
FIG. 1 is a schematic diagram of an exemplary medical device suitable for practicing the present invention.

FIG. 1 is a schematic diagram of an exemplary medical device suitable for practicing the present invention. As illustrated in FIG. 1, a medical device according to the present invention may include an ICD 10 coupled to a patient's heart by way of three leads 6, 15, and 16, for example. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, a tip electrode 26, and a coil electrode 20, each of which are connected to an insulated conductor contained within the body of lead 16. The proximal end of the insulated conductors are coupled to corresponding connectors carried by a connector assembly 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and a tip electrode 17 for sensing and pacing in the right atrium. Lead 15 is further equipped with a coil electrode 23 for delivering high-energy shock therapy. The ring electrode 21, the tip electrode 17 and the coil electrode 23 are each connected to an insulated conductor with the body of the right atrial lead 15. Each insulated conductor is coupled at its proximal end to a connector within connector assembly 13 adapted for electrical connection to ICD 10.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles.

During T-shock delivery methods provided by the present invention, the right ventricular tip electrode 24 is used with either ring electrode 26 or housing 11 to deliver a primary S1 pacing pulse train to the ventricles to facilitate timing of a T-shock during the vulnerable period. Any of the available ventricular electrodes 24 and 26, coil electrodes 8, 20 and 23, and housing 11 may be used in various unipolar or bipolar sensing configurations for obtaining one or more EGM signals during S1 pacing train delivery for use in validating the S1 train. A T-shock is delivered using any of the coil electrodes 8, 20, or 23 and may utilize the device housing 11 as a "can" electrode.

It is recognized that alternate lead systems may be substituted for the three lead system illustrated in FIG. 1. Any available ventricular pacing and sensing electrodes may be used for delivering and validating the S1 train according to the methods described in detail below, and any available high-voltage electrodes may be used for delivering the T-shock as well as for sensing EGM signals for S1 train validation.

In some embodiments, subcutaneous electrodes may be provided and used for applying S1 pacing pulses and T-shocks. For example, stimulation may be delivered using the "can" electrode and a subcutaneous electrode carried by a lead extending from the ICD. Subcutaneous electrode pairs may be incorporated in or on the ICD housing or provided on a subcutaneous lead and could be used for sensing intrinsic ventricular events and evoked responses. In alternative embodiments, a hybrid system including subcutaneous electrodes and either transvenous electrodes or epicardial electrodes may be used. For example, transvenous leads may be used to position electrodes within the heart for accurate sensing of cardiac activity and evoked responses during S1 pacing train delivery, and subcutaneous electrodes may be positioned for delivering S1 pacing pulses and T-shocks.

The invention may alternatively be implemented in a "leadless" implantable device. Reference is made, for example, to the subcutaneous ICD generally disclosed in U.S. Pat. No. 6,647,292, issued to Bardy et al., incorporated herein by reference in its entirety. In such a system, the S1 pacing train could be delivered through a subcutaneous defibrillation pathway and the same electrodes or alternate electrodes implanted subcutaneously could be used for sensing an evoked response following the S1 pulses. In any of these various embodiments, the methods provided herein would increase the likelihood that a T-shock would induce VF for DFT testing and would promote reliable ULV measurements.

While a particular multi-chamber ICD and lead system is illustrated in FIG. 1, methodologies provided by the present invention may be adapted for use with other single chamber, dual chamber, or multichamber ICD systems. Atrial chamber sensing and stimulation capabilities are not necessary for practicing the invention.

Figure 2:
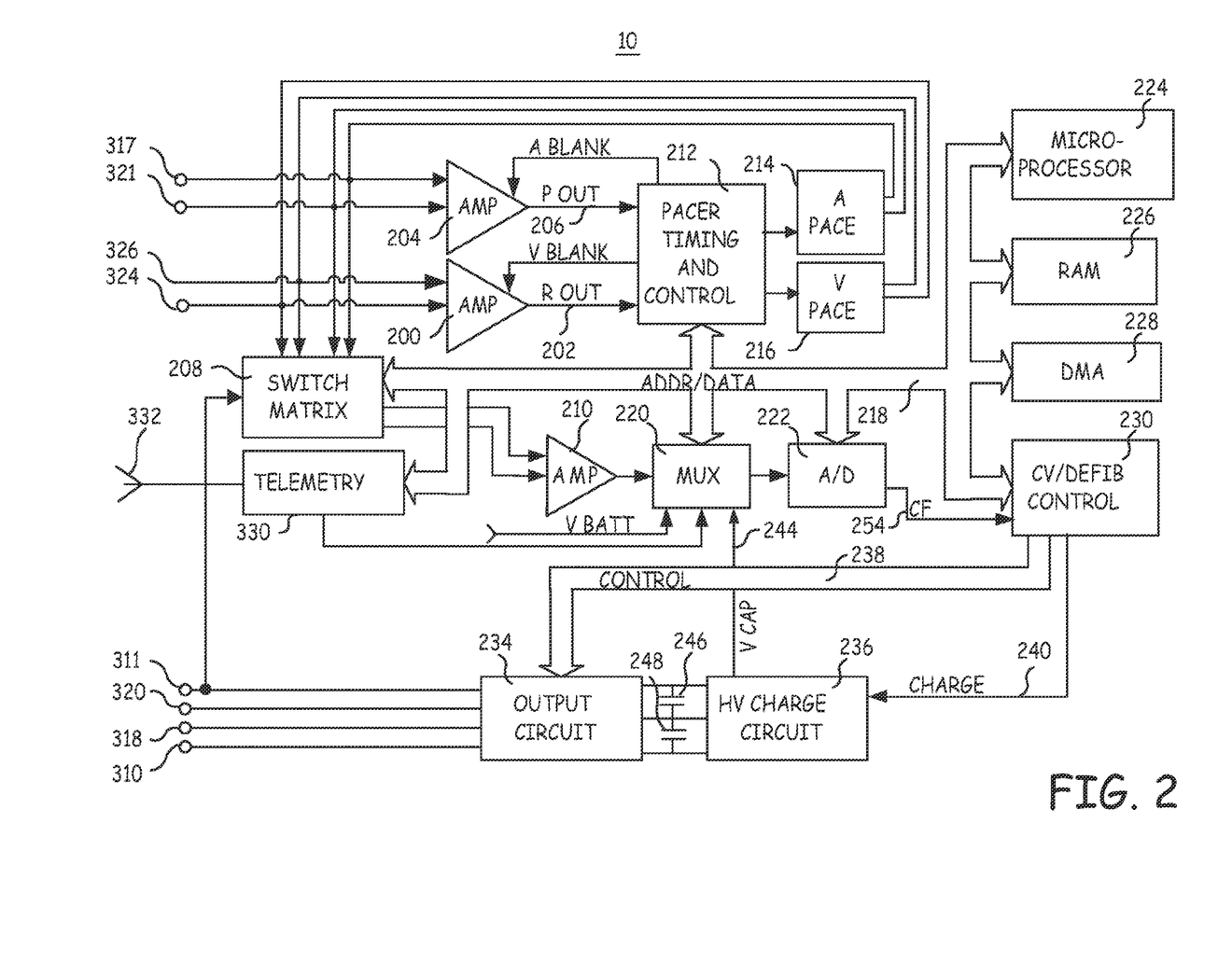
FIG. 2 is a functional block diagram of the medical device of FIG. 1.

FIG. 2 is a functional block diagram of the medical device of FIG. 1. This functional diagram is exemplary of the type of device in which the invention may be implemented, however, the invention may usefully be practiced in a variety of device implementations, including devices used for electrophysiological studies, implantable or external devices which deliver electrical stimulation therapies, and implantable or external devices which deliver other forms of cardiac rhythm therapies such as nerve stimulation or drug administration. The disclosed embodiment shown in FIG. 2 is a microprocessor-controlled device, but the methods of the present invention may also be practiced with devices employing dedicated analog or digital circuitry for controlling device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the tip electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 may be embodied as automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

In accordance with the present invention, generation of a signal on R-out signal line during an ER sensing window can be used in verifying capture of an S1 pacing pulse. Capture verification of at least the last S1 pacing pulse is used in validating an S1 pacing train.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228.

Microprocessor 224 may employ the digitized EGM signals stored in random access memory 226 in conjunction with S1 capture verification methods for validating an S1 train in accordance with the present invention. For example, the microprocessor 224 may analyze a ventricular EGM signal acquired following an S1 pulse or verifying capture of the S1 pulse. In one embodiment, digitized EGM signals are used to sense a ventricular event occurring during an ER sensing window following an S1 pacing pulse to verify capture of the S1 pacing pulse. In another embodiment, the morphology of a digitized sensed event signal following an S1 pulse is compared to a previously determined ER morphology stored in RAM 226 for verifying that the sensed event is an actual ER and not an intrinsic event. In another embodiment, the temporal relationship of sensed events occurring on different EGM sources following an S1 pulse is compared to a known ER temporal relationship for verifying that the sensed events represent an actual ER to the S1 pulse. The operation of the microprocessor 224 in performing the S1 train validation methods provided by the present invention can be controlled by executable software stored in ROM, associated with microprocessor 224.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit 330 are provided by microprocessor 224 via address/data bus 218. Received telemetry is provided to microprocessor 224 via multiplexer 220. Any type of telemetry system known for use in implantable devices may be used.

The remainder of circuitry illustrated in FIG. 2 is dedicated to the provision of cardiac pacing, cardioversion and defibrillation therapies. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing. In accordance with the present invention, pacer timing and control circuitry 212 is used to control the delivery of an S1 pacing train at an overdrive rate, slightly greater than a sensed intrinsic heart rate.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and used in conjunction with the present invention to diagnose the occurrence of a variety of arrhythmias.

Microprocessor 224 operates as an interrupt driven device, and is responsive to interrupts from pacer timing and control circuitry 212 corresponding to the occurrences of sensed P-waves and R-waves and corresponding to the generation of cardiac pacing pulses. These interrupts are provided via data address bus 218. Any necessary mathematical calculation or logic operations to be performed by microprocessor 224, including those to be described in greater detail below, and any updating of values or intervals controlled by pacer timing and control circuitry 212 take place following such interrupts. These operations are performed under the control of software stored in ROM associated with microprocessor 224. A portion of the random access memory 226 may be configured as a number of recirculating buffers capable of holding a series of measured intervals, which may be analyzed in response to a pace or sense interrupt by microprocessor 224 for diagnosing an arrhythmia.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart by high voltage output circuit 234 under the control of the pacer timing and control circuitry 212 via a control bus 238. The output circuit 234 determines the electrodes used for delivering the cardioversion or defibrillation pulse and the pulse wave shape. Examples of high-voltage cardioversion or defibrillation output circuitry are generally disclosed in U.S. Pat. No. 4,727,877 issued to Kallok, and U.S. Pat. No. 5,163,427 issued to Keimel, both incorporated herein by reference in their entirety.

During T-shock delivery, used for example, for VF inductions, DFT measurements or ULV measurements, pacer timing and control circuitry 212 controls the delivery of an S1 train while cardioversion and defibrillation control circuitry 230 initiates charging of the high voltage capacitors 246 and 248 for T-shock delivery. The pacer timing and control circuitry controls the delivery of a T-shock by output circuit 234 following the last S1 pacing pulse at a predetermined pace-T-shock interval. The pace-T-shock interval is set based on a previous measurement of the time between an S1 pacing pulse and a subsequently sensed T-wave or other measurement of the patient's refractory period or Q-T interval. Methods for delivering a train of overdrive pacing pulses followed by a T-shock at a predetermined pace-T-shock interval may be implemented according to methods known in the art, for example as generally disclosed in U.S. Pat. No. 5,129,392 issued to Bardy, et al, incorporated herein by reference in its entirety. As will be described in greater detail below, the present invention provides a method for validating the S1 train to increase the likelihood that the T-shock has been properly delivered during the vulnerable period.

Figure 3:
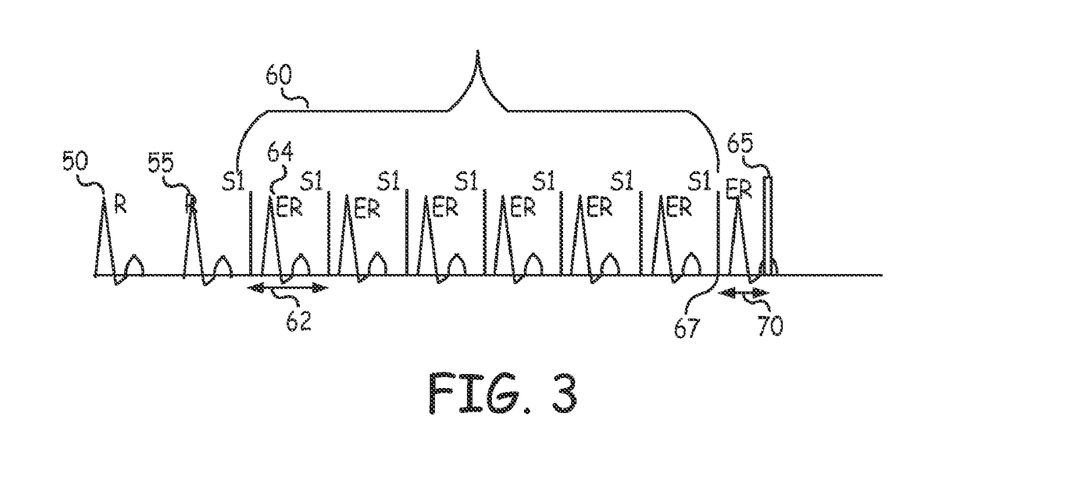
FIG. 3 is a timing diagram illustrating the delivery of an S1 pacing train and subsequent T-shock.

FIG. 3 is a timing diagram illustrating the delivery of an S1 pacing train and subsequent T-shock. Intrinsic R-waves 50 and 55 are sensed at the intrinsic heart rate by the ICD ventricular sensing circuitry. Timing and control circuitry will set the S1 pacing train interval 62 such that the S1 pacing rate will be greater than the intrinsic ventricular rate. A train of S1 pulses 60 are delivered at the overdrive pacing rate corresponding to interval 62. The S1 pulses are set to a pulse amplitude and width that is above the pacing threshold required to capture the ventricle. The pacing threshold is determined previously using threshold testing methods known in the art.

In the illustration of FIG. 3, each of the S1 pulses are followed by an evoked response (ER) 64 indicating that the S1 pulses have successfully captured the ventricle. Following the last S1 pulse 67, a T-shock 65 is delivered at a pace-T-shock interval 70 previously set such that the T-shock will be delivered during the vulnerable period following the last S1 pulse. The T-shock will have a high probability of being coupled to the cardiac cycle during the vulnerable period when each of the S1 pulses of S1 train 60 has captured the ventricle. If any of the S1 pulses do not capture the ventricle, in particular if the last S1 pulse 67 does not capture, or if an intrinsic ventricular event occurs prior to T-shock delivery, the refractoriness of the heart may be altered such that the pace-T-shock interval 70 is not valid in ensuring that the T-shock 65 occurs during the vulnerable period.

As such, the invention provides an apparatus and method for validating the S1 train 60 to increase the likelihood that the T-shock is delivered during the vulnerable period. As will be described below, S1 train validation includes verifying capture of at least the last S1 pulse 67 and may include verifying capture of any portion or all of the S1 pulses. The S1 train validation method further includes sensing for any intervening intrinsic ventricular events that could alter the timing of the refractory period relative to the last S1 pulse 67. In particular, intrinsic ventricular events that occur after the last S1 pulse and prior to T-shock delivery will invalidate the S1 train. In some embodiments, intrinsic events occurring during the S1 train prior to the last S1 pulse 67 may also invalidate the S1 train.

Figure 4:
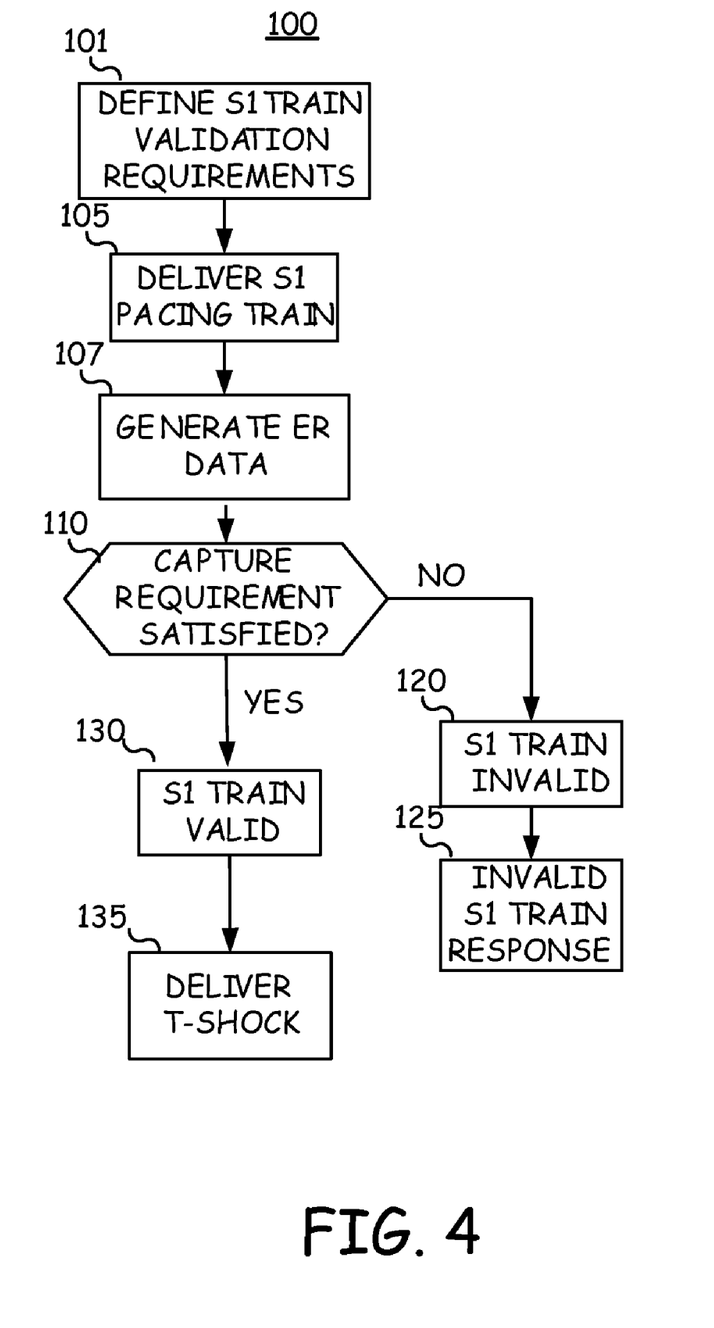
FIG. 4 is a flow chart of a method of validating a pacing train associated with the delivery of a high-energy pulse in a medical device according to the present invention.

FIG. 4 is a flow chart of a method of validating a pacing train associated with the delivery of a high-energy pulse in a medical device according to the present invention. The steps included, in the various methods described herein may be incorporated in software or firmware executed by a microprocessor for controlling ICD, AED or other appropriate medical device functions. Some functions performed during execution of the methods described herein may be embodied in dedicated integrated circuitry.

As illustrated in FIG. 4, a method 100 of validating a pacing train according to the present invention includes defining an S1 train validation requirement, step 101. The S1 validation requirement includes an S1 capture requirement and may include requirements regarding intrinsic ventricular event sensing. In one embodiment, the S1 capture requirement for validating an S1 train requires capture by the last S1 pacing pulse prior to scheduled T-shock delivery. In other embodiments, capture by a selected portion of the S1 pulses including the last S1 pulse is required to validate the S1 train. Alternatively, capture verification operations, which generally includes ER sensing and may include other methods as described below, are performed following all S1 pulses, and a minimum number of the S1 pulses, including the last S1 pulse, are required to capture the ventricles in order to validate the S1 train. The minimum number of S1 pacing pulses required to capture the ventricles may be all of the S1 pacing pulses.

The S1 train validation requirement defined at step 101 may further include a requirement that no intrinsic ventricular events occur prior to T-shock delivery. In one embodiment, in order for the S1 pacing train to be valid, no intrinsic events may occur between the last S1 pulse and T-shock delivery, i.e. during the pace-T-shock interval. In other embodiments, intrinsic events sensed at any time during the S1 pacing train will cause the S1 train to be determined to be invalid.

At step 105, an S1 pacing train is delivered. The S1 pacing train may be delivered during electrophysiological testing for the purposes of VF induction, a DFT measurement or during ULV testing. The methods provided by the invention for validating an S1 train are valuable during ULV testing since a failure to induce VF could be due to a T-shock greater than the ULV but could also be due to delivery of the T-shock outside of the vulnerable zone. By validating the S1 train, the clinician can be relatively confident that the T-shock was delivered within the vulnerable period and a failure to induce indicates the T-shock energy is greater than the ULV. If the S1 train is invalidated, and a T-shock was delivered but failed to induce VF, the test may be repeated until the S1 train is validated.

During DFT testing, validation of the S1 train is useful to the clinician in minimizing the time required for the testing. If a T-shock fails to induce, the clinician may spend time adjusting the pace-T-shock interval or adjusting the T-shock energy in order to successfully induce VF. However, the failure to induce may have been the result of an invalid S1 train and the T-shock energy and the pace-T-shock interval that were used may have been appropriate for VF induction if the S1 train had been valid. A clinician may spend time making adjustments to the T-shock energy or pace-T-shock interval that then cause the T-shock to fail to induce VF following a valid S1 train. Validating the S1 train can therefore save time during DFT testing by preventing unnecessary adjustments of the T-shock energy or pace-T-shock interval. If an S1 train is found to be invalid, the S1 train can be repeated until it is valid. As such, the general method summarized by FIG. 4 is applicable to ULV testing and DFT testing or any other clinical testing performed which involves T-shock delivery following a pacing train.

During delivery of the S1 pacing train, evoked response data is generated, step 107, that is utilized to verify capture of either all of the delivered S1 pacing pulses, at least the last S1 pacing pulse of the delivered S1 pacing train, or any desired portion of the S1 pacing pulses of the delivered S1 pacing train. The capture verification data may correspond to evoked response morphology, temporal consistency of the evoked response, or cross correlation of the sensing of the evoked response from multiple EGM sources, for example, as will be described below. A determination is then made, based on the generated evoked response data, as to whether associated capture requirements defined at step 101 are satisfied, step 110.

If the capture requirements are not satisfied, the S1 train is declared invalid at step 120. For example, if the last S1 pacing pulse results in loss of capture, the S1 train is invalid.

If the S1 train capture requirements are satisfied, the S1 train is declared valid at step 130. A T-shock may be delivered at step 135 at a predetermined pace-T-shock interval in response to the valid S1 pacing train.

According the present invention, if the S1 train capture requirements are not satisfied in step 110, and therefore the S1 train is determined to be invalid, step 120, an invalid S1 train response is initiated, step 125. The invalid S1 train response can include any of, but is not limited to: withholding a scheduled T-shock, extending the S1 pacing pulse train, repeating the S1 pacing pulse train, adjusting the S1 pacing parameters such as rate or pulse energy, and/or generating an alert signal or displayed message on an external programmer to notify a clinician or other user that the S1 train is invalid. The clinician is thereby informed that the response to a delivered T-shock following the invalid S1 train is unreliable for ULV or DFT measurements and can choose to repeat T-shock tests as necessary.

Figure 5:
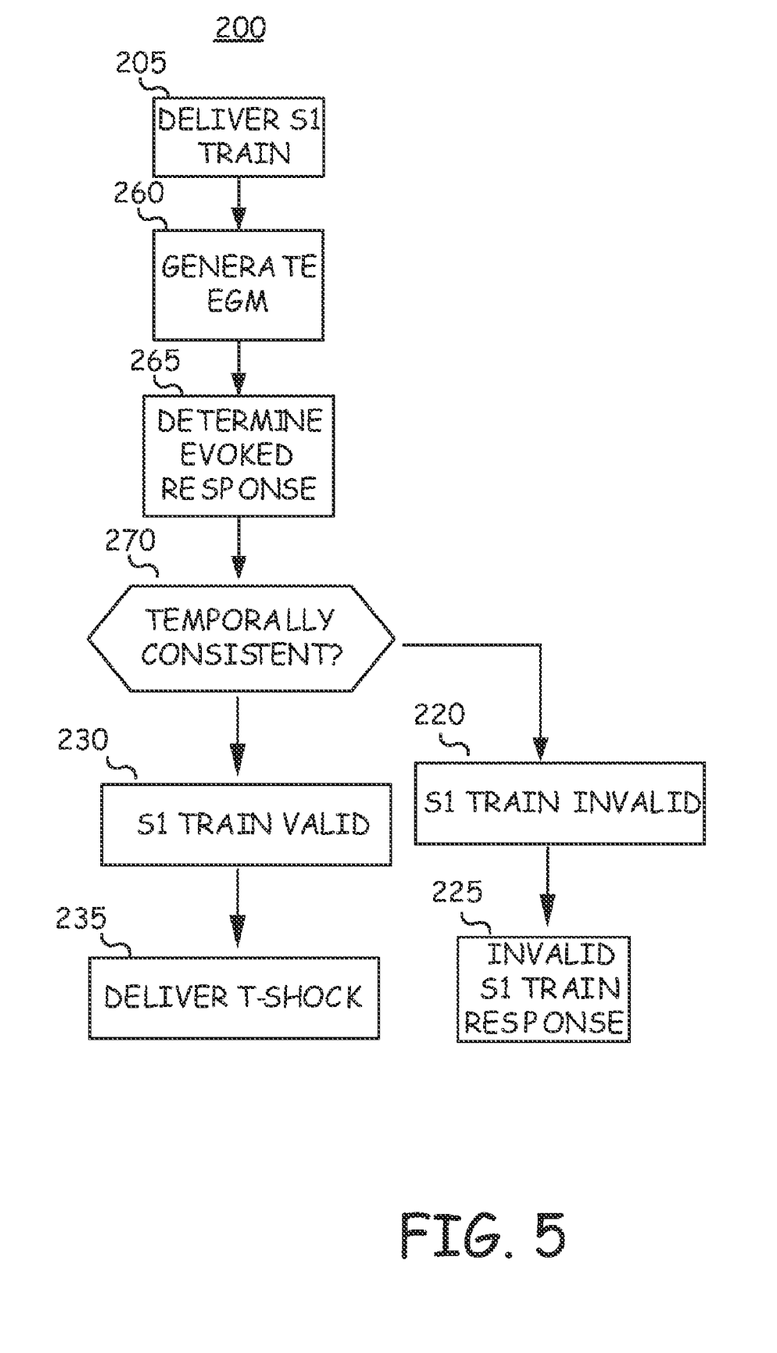
FIG. 5 a flow chart of a method of validating a pacing train associated with the delivery of a high-energy pulse in a medical device according to an embodiment of the present invention.

FIG. 5 a flow chart of a method of validating a pacing train associated with the delivery of a high-energy pulse in a medical device according to an embodiment of the present invention. According to the present invention, capture verification of S1 pacing pulses may include either sensing of an evoked response during a predetermined sensing window during delivery of the S1 pulse train to determine the temporal consistency of the evoked response, verifying that a sensed event occurring after an S1 pulse is an actual evoked response using morphological analysis of the sensed event, or evaluating the temporal relationship between events corresponding to sensing of the evoked response at different EGM sensing locations following an S1 pulse. In addition, capture verification of the S1 pacing pulses may include any combination or all three of determining the temporal consistency of the evoked response, determining the evoked response morphology, and evaluating the temporal relationship of sensing of the evoked response from multiple sensing locations.

As illustrated in FIG. 5, in an embodiment in which capture verification includes the determination of the temporal consistency of the evoked response, an S1 pacing train is delivered, step 205, and an EGM signal corresponding to each of the pulses associated with the delivered S1 pacing train is generated from signals sensed between electrodes 24 and 26, for example, step 260. An evoked response is determined for each EGM signal, step 265, and the evoked responses are compared to determine whether they are temporally consistent, step 270. For example, the time interval of the evoked response associated with the second evoked response is compared to the time interval of the evoked response associated with the first delivered pulse, the time interval of the evoked response associated with the third delivered pulse is compared to the time interval of the evoked response associated with the second delivered pulse, and so forth.

Once the time interval of the final evoked response is compared to the time interval of the previous evoked response, the determination as to whether the evoked responses are temporally consistent is made, step 270, by determining whether the time interval of one of the evoked responses differs from the previous time interval by more than a predetermined time period, such as 10 ms, for example, although any desired time interval could be utilized. Other methods of determining the temporal consistency may also be utilized. For example, the evoked responses may be determined not to be temporally consistent only after the time intervals of more than one of the evoked response differs by more than the predetermined time period.

In addition, according to an embodiment of the present invention, since the likelihood that the pacing train may be an invalid pacing train increases if the temporal inconsistency occurs for an evoked response that is positioned in close proximity to the last delivered pulse compared to when the temporal inconsistency occurs for an evoked response positioned in further proximity to the last delivered pulse, i.e., closer to the first delivered pulse, the determination of the temporal consistency includes assigning a weighting factor to intervals that differ by more than the predetermined time period based upon where in the delivered pulse train the inconsistent pulse occurs. For example, the pulse train is determined to be invalid when the pulse having the time interval that differs from the previous pulse by more than the predetermined time period is positioned at least a predetermined number of pulses or less from the last pulse, such as three for example. According to an embodiment of the present invention, the pulse train may be determined to be invalid only in response to the time interval associated with the last pulse differing from the previous pulse by more than the predetermined time period.

Other methods for determining the temporal consistency of the pulse may also be utilized, such as a combination of the proximity of the evoked response in the pulse train and the number of evoked response intervals that are temporally inconsistent. In addition, it is understood that other methods could be utilized to determine the temporal inconsistency in place of comparing the interval to a previous interval, such as taking an average of the determined evoked response intervals, for example.

If the S1 train is determined to be temporally consistent, the S1 train is identified as being a valid pulse train, step 230, and a T-shock may be delivered, step 235, at a predetermined pace-T-shock interval in response to the valid S1 pacing train.

According the present invention, if the S1 train is determined not to be temporally consistent, the S1 train is determined to be invalid, step 220, and an invalid S1 train response is initiated, step 225. The invalid S1 train response can include any of, but is not limited to: withholding a scheduled T-shock, extending the S1 pacing pulse train, repeating the S1 pacing pulse train, withholding delivery of the pacing train, adjusting the S1 pacing parameters such as rate or pulse energy, and/or generating an alert signal or displayed message on an external programmer to notify a clinician or other user that the S1 train is invalid. The clinician is thereby informed that the response to a delivered T-shock following the invalid S1 train is unreliable for ULV or DFT measurements and can choose to repeat T-shock tests as necessary.

Figure 6:
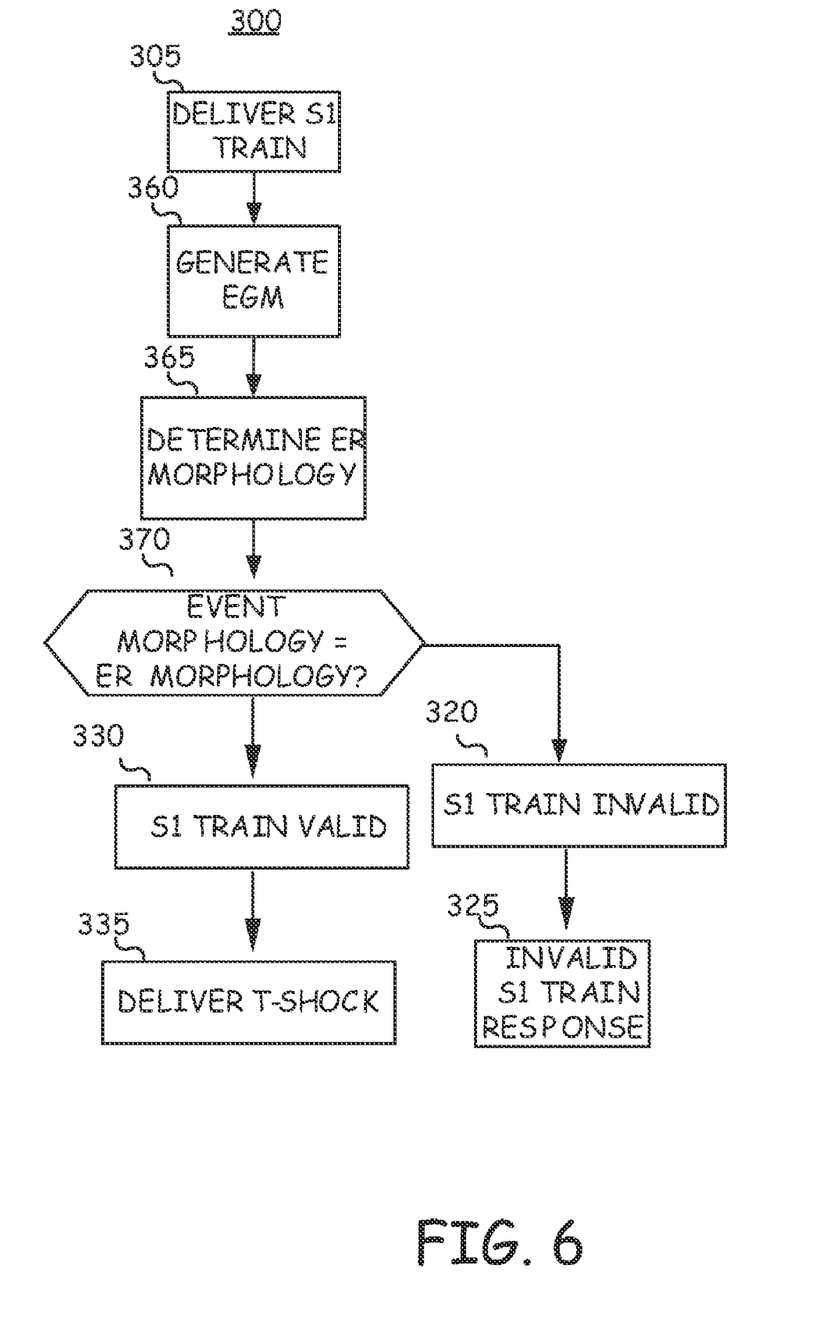
FIG. 6 a flow chart of a method of validating a pacing train associated with the delivery of a high-energy pulse in a medical device according to an embodiment of the present invention.

FIG. 6 a flow chart of a method of validating a pacing train associated with the delivery of a high-energy pulse in a medical device according to an embodiment of the present invention. As illustrated in FIG. 6, in an embodiment in which capture verification includes the determination of the morphology of the evoked response, an S1 pacing train is delivered, step 305, and an EGM signal corresponding to each of the pulses associated with the delivered S1 pacing train is generated from signals sensed between electrodes 24 and 26, for example, step 360. The morphology of each of the acquired evoked response signals is determined, step 365 and compared to a predetermined morphology template to determine whether the morphology of the individual evoked responses correlate with the morphology template, step 370. In this way, a determination is made as to whether the sensed evoked response corresponds to an intrinsic event and is therefore not a valid evoked response resulting from the associated delivered pulse.

According to the present invention, the morphology parameter may be any evoked response signal feature, such as peak amplitude, signal width, peak slope, or a template of the evoked response signal. Alternatively, determination of an evoked response morphology parameter may include wavelet transform or Fourier Transform analysis. Methods are known in the art for performing morphological comparisons of EGM signals. For example, comparison of digitized EGM signals using wavelet transform analysis is generally described in U.S. Pat. No. 6,393,316 issued to Gillberg, et al., incorporated herein by reference in its entirety. In addition, the morphology parameter may correspond to an intrinsic event, and therefore the evoked response morphologies are compared to the intrinsic event morphology to determine whether the evoked response is associated with the intrinsic event and is therefore not a valid evoked response resulting from the associated delivered pulse.

If the morphology of the evoked response for one of the delivered pulses is determined to be not approximately equal to the morphology template, i.e., the sensed evoked response corresponds to an intrinsic event, the S1 train is identified as being an invalid pulse train, step 320.

Other methods of using morphology may also be utilized. For example, the S1 pulses train could be determined to invalid only after the morphology of more than one of the sensed evoked responses is determined to be not approximately equal to the morphology template. In addition, according to an embodiment of the present invention, since the likelihood that the pacing train may be an invalid pacing train increases if the intrinsic event occurs for a pulses that is positioned in close proximity to the last delivered pulse compared to when the intrinsic event occurs for a delivered pulse positioned in further proximity to the last delivered pulse, i.e., closer to the first delivered pulse, the determination of the morphology of the evoked response includes assigning a weighting factor to the determined invalid pulses based upon where in the delivered pulse train the intrinsic event occurs. For example, the pulse train is determined to be invalid when the pulse associated with the determined intrinsic event is positioned at least a predetermined number of pulses or less from the last pulse, such as three for example. According to an embodiment of the present invention, the pulse train may be determined to be invalid only in response to the last pulse being determined to be an intrinsic event.

Other methods for determining the validity of the pulse train based on evoked response morphology may also be utilized, such as a combination of the proximity of the pulse associated with an intrinsic event in the pulse train and the number of evoked responses that do not matches the morphology template, i.e., are determined to be intrinsic events.

According the present invention, once the S1 train is identified as being invalid, step 320, an invalid S1 train response is initiated, step 325. The invalid S1 train response can include any of, but is not limited to: withholding a scheduled T-shock, extending the S1 pacing pulse train, repeating the S1 pacing pulse train, withholding delivery of the pacing pulse train, adjusting the S1 pacing parameters such as rate or pulse energy, and/or generating an alert signal or displayed message on an external programmer to notify a clinician or other user that the S1 train is invalid. The clinician is thereby informed that the response to a delivered T-shock following the invalid S1 train is unreliable for ULV or DFT measurements and can choose to repeat T-shock tests as necessary.

If the morphology of each of or of the predetermined ones of the evoked responses associated with the delivered pulses is determined to be approximately equal to the morphology template, i.e., none of the sensed evoked responses correspond to an intrinsic event, or none that are located in the predetermined location of the pulse train are determined to correspond to an intrinsic event, the S1 train is identified as being a valid pulse train, step 330, and a T-shock may be delivered, step 335, at a predetermined pace-T-shock interval in response to the valid S1 pacing train.

Figure 7:
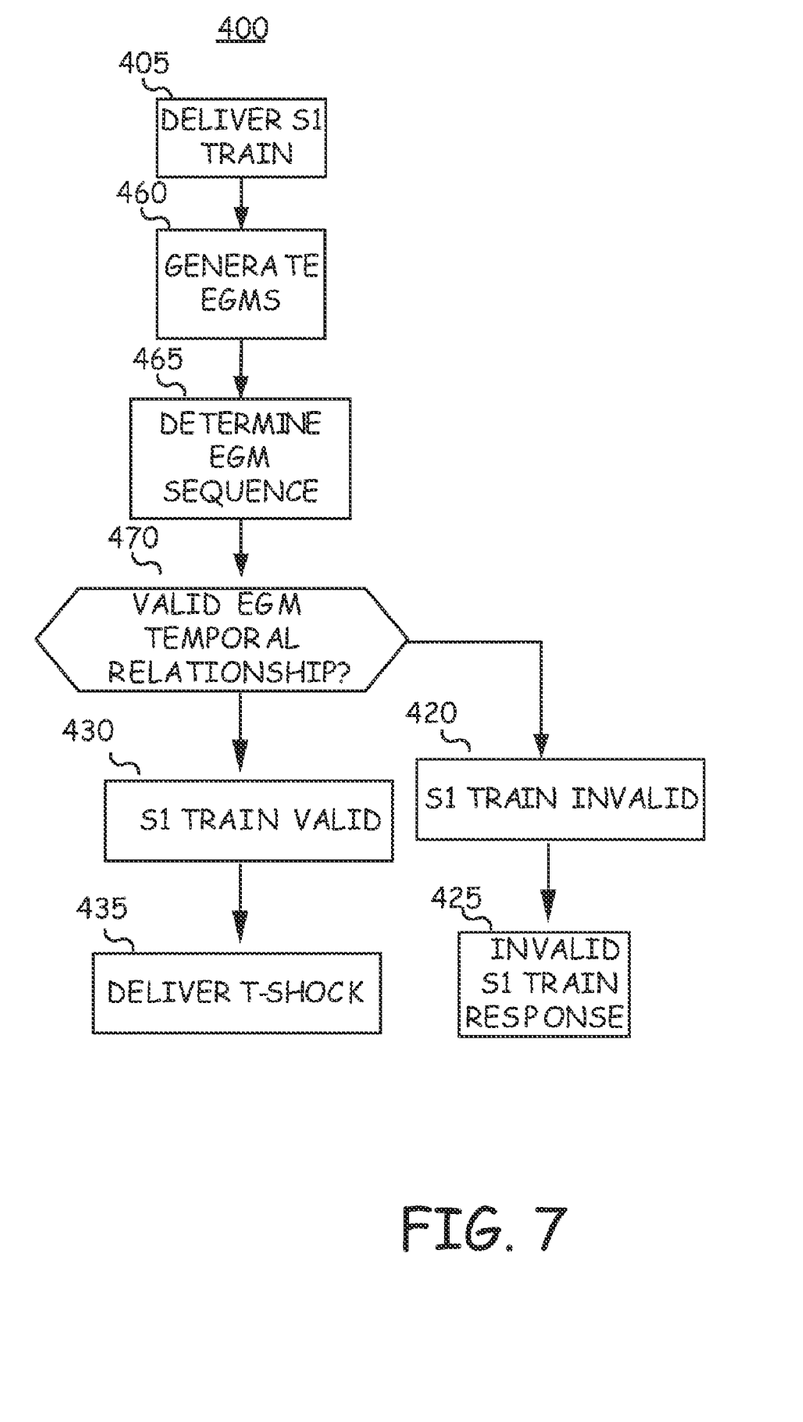
FIG. 7 a flow chart of a method of validating a pacing train associated with the delivery of a high-energy pulse in a medical device according to an embodiment of the present invention.

FIG. 7 a flow chart of a method of validating a pacing train associated with the delivery of a high-energy pulse in a medical device according to an embodiment of the present invention. As illustrated in FIG. 7, in an embodiment in which capture verification includes the determination of the temporal relationship of sensing of the evoked response from multiple sensing locations, an S1 pacing train is delivered, step 405, and an EGM signal corresponding to each of the pulses associated with the delivered S1 pacing train is generated from signals sensed at two or more sensing locations, step 460, such as between electrodes 24 and 26 positioned along lead 16 and electrodes positioned along coronary sinus lead 6, for example. Based on the EGM signals, a determination of the sequence of the EGM signals is made, step 465, and based on the EGM sequence, a determination is made as to whether the temporal relationship of the EGM signals sensed from different locations is valid, step 470. According to the present invention, if the evoked response results from the delivered pacing pulse, rather than an intrinsic event, the evoked response will be sensed by the sensing electrode positioned within the apex of the right ventricle prior to being sensed by the electrode positioned along the coronary sinus and the left ventricle. Therefore, the temporal relationship of the sensed EGM signals will be determined to be valid if the evoked response is sensed at the right ventricle prior to being sensed at the left ventricle, and invalid if the evoked response is sensed at the left ventricle prior to being sensed at the right ventricle.

If the S1 train is determined to be associated with a valid EGM temporal relationship, the S1 train is identified as being a valid pulse train, step 430, and a T-shock may be delivered, step 435, at a predetermined pace-T-shock interval in response to the valid S1 pacing train.

According the present invention, if the S1 train is determined not to be associated with a valid EGM temporal relationship, the S1 train is determined to be invalid, step 420, and an invalid S1 train response is initiated, step 425. The invalid S1 train response can include any of, but is not limited to: withholding a scheduled T-shock, extending the S1 pacing pulse train, repeating the S1 pacing pulse train, adjusting the S1 pacing parameters such as rate or pulse energy, and/or generating an alert signal or displayed message on an external programmer to notify a clinician or other user that the S1 train is invalid. The clinician is thereby informed that the response to a delivered T-shock following the invalid S1 train is unreliable for ULV or DFT measurements and can choose to repeat T-shock tests as necessary.

Figure 8:
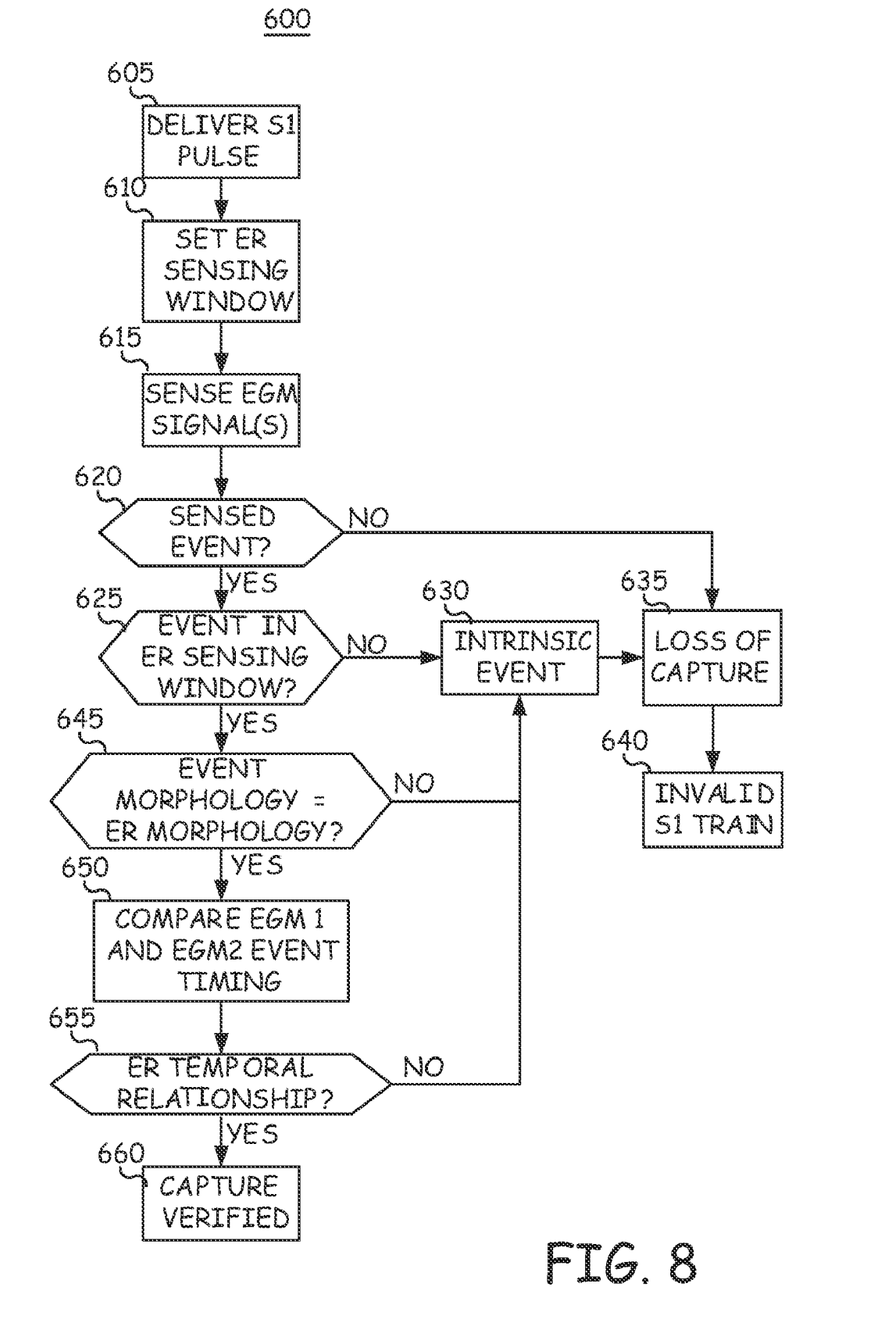
FIG. 8 a flow chart of a method of validating a pacing train associated with the delivery of a high-energy pulse in a medical device according to an embodiment of the present invention.

According to the present invention, capture verification for a delivered pulse train may be performed using only one of the pulse train validation techniques described above, or any combination of two or more of the pulse train validation techniques. FIG. 8 a flow chart of a method of validating a pacing train associated with the delivery of a high-energy pulse in a medical device according to an embodiment of the present invention. As illustrated in FIG. 8, a method 600 of validating a pacing train associated with the delivery of a high-energy pulse in a medical device according to an embodiment of the present invention is performed during the delivery of an S1 pacing train for validation of the S1 train during DFT or ULV measurements. Capture verification method 600 may be performed in response to the last S1 pacing pulse or in response to any selected portion or all of the S1 pacing pulses, in accordance with a previously defined capture requirement for S1 train validation.

After delivery of an S1 pacing pulse at step 605 for which capture verification is required, an ER sensing window is set at step 610. The selected EGM sources are sensed at step 615, which may include sensing of one or more EGM sources. At decision step 620, method 600 determines if an event is sensed from the EGM signal(s). ER sensing circuitry and methods may be generally implemented according to methods known in the art. If no events are sensed following the S1 pulse, loss of capture is declared at step 635. The S1 train may be declared invalid at step 640 according to the S1 capture requirements.

If an event is sensed at step 620, method 600 determines if the event occurred during the ER sensing window, step 625. If the sensed event occurs outside the ER sensing window, the event is declared an intrinsic event, step 630. If no event is sensed within the ER sensing window and an intrinsic event is sensed outside the ER sensing window, loss of capture is declared, step 635. The S1 train may be declared invalid at step 640 depending on the S1 capture requirements.

If the sensed event does occur within the ER window as determined at step 625, a morphological comparison of the sensed event and a previously stored ER morphology parameter or template is performed, step 645. If the sensed event morphology is not substantially equal to the stored ER morphology, the sensed event is declared an intrinsic event, step 630. Loss of capture is declared, step 635, and the S1 pacing train may be declared invalid, step 640 depending on the S1 capture requirements.

If the sensed event morphology is substantially equal to the previously stored ER morphology, the temporal relation between sensed events occurring on different EGM signal sources is determined by comparing the timing of the sensing of the event at the EGM sources, step 650, and a determination is made as to whether a temporal relationship between the sensing of the event at the EGM sources is substantially equal to the ER temporal relationship determined and stored previously, step 655. If the temporal relation between the sensed events on different EGM sources is not substantially equal to the ER temporal relationship determined and stored previously, the event is declared an intrinsic event, step 630. Loss of capture is declared, step 635, and the S1 train may be determined to be invalid, step 640 depending on the S1 capture requirement. If the temporal relation between sensed events on different EGM sources is substantially equal to the previously determined ER temporal relationship, as determined at step 655, capture is declared, step 660. The S1 pacing train may be declared valid if all S1 pulses for which capture verification is required are determined to capture the ventricle and no invalidating intrinsic events are sensed as described previously.

In some embodiments, ventricular capture by an S1 pulse may be verified based on sensing a ventricular event during an ER sensing window. In other embodiments, capture verification includes any combination of sensing an event during an ER sensing window, matching the sensed event morphology to a previously stored ER morphology, and matching the temporal relation between sensed events on multiple EGM signals to a previously determined ER temporal relation. Any combination of these capture verification techniques may be used following one or more S1 pulses to determine if the S1 pacing train capture requirement is met.

Some of the techniques described above may be embodied as a computer-readable medium comprising instructions for a programmable processor such as a microprocessor. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus, an apparatus and method for validating an S1 pacing train that precedes T-shock delivery has been described. The embodiments described herein are intended to illustrate the various aspects of the invention. It is recognized that one having skill in the art and the benefit of the teachings provided herein may conceive of numerous modifications to the described embodiments. The embodiments described are intended to be exemplary, not limiting, with regard to the following claims.

What is claimed is:

1. A medical device capable of generating a pacing pulse train associated with delivery of a high-energy pulse, comprising:
   means for delivering the pacing pulse train to a chamber of a patient's heart;
   means for generating evoked response data associated with the delivered pacing pulse train;
   means for determining, in response to the generated evoked response data, whether one or more predetermined pacing pulse train requirements are satisfied and identifying the pacing pulse train as being valid in response to the one or more requirements being satisfied; and
   means responsive to the identification of the pacing train as valid for delivering the high-energy pulse to the chamber of the patient's heart at a predetermined delay following delivery of the pacing pulse train, wherein the means for determining whether one or more predetermined pacing pulse train requirements are satisfied compares the generated evoked response data, determines a temporal consistency of the compared evoked response data, determines whether time intervals associated with a plurality of evoked responses corresponding to the pacing pulse train differ by more than a predetermined time period, wherein the means for determining whether one or more predetermined pacing pulse train requirements are satisfied determines one or more locations of temporally inconsistent evoked response data along the delivered pacing pulse train, and wherein the means for determining whether one or more predetermined pacing pulse train requirements are satisfied assigns one or more weighting factors in response to the determined one or more locations.

2. A medical device capable of generating a pacing pulse train associated with delivery of a high-energy pulse, comprising:
   means for delivering the pacing pulse train to a chamber of a patient's heart;
   means for generating evoked response data associated with the delivered pacing pulse train;
   means for determining, in response to the generated evoked response data, whether one or more predetermined pacing pulse train requirements are satisfied and identifying the pacing pulse train as being valid in response to the one or more requirements being satisfied; and means responsive to the identification of the pacing train as valid for delivering the high-energy pulse to the chamber of the patient's heart at a predetermined delay following delivery of the pacing pulse train, wherein the means for determining whether one or more predetermined pacing pulse train requirements are satisfied compares the generated evoked response data, determines a temporal consistency of the compared evoked response data, determines whether time intervals associated with a plurality of evoked responses corresponding to the pacing pulse train differ by more than a predetermined time period, and wherein the pacing pulse train includes a last pacing pulse and the means for determining whether one or more predetermined pacing train requirements are satisfied determines whether temporally inconsistent evoked response data corresponds to the last pacing pulse.

3. A medical device capable of generating a pacing pulse train associated with delivery of a high-energy pulse, comprising:

means for delivering the pacing pulse train to a chamber of a patient's heart;

means for generating evoked response data associated with the delivered pacing pulse train;

means for determining, in response to the generated evoked response data, whether one or more predetermined pacing pulse train requirements are satisfied and identifying the pacing pulse train as being valid in response to the one or more requirements being satisfied; and means responsive to the identification of the pacing train as for delivering the high-energy pulse to the chamber of the patient's heart at a predetermined delay following delivery of the pacing pulse train, wherein the means for determining whether one or more predetermined pacing pulse train requirements are satisfied determines morphology of an evoked response in response to the evoked response data and compares the determined morphology to a predetermined evoked response morphology template.

4. The device of claim 3, wherein the requirements include one of evoked response morphology, temporal consistency of the evoked response, and cross correlation of sensing of the evoked response from multiple sensing locations.

5. The device of claim 3, wherein the means for determining whether one or more predetermined pacing train requirements are satisfied determines whether a predetermined number of determined morphologies associated with the delivered pacing pulse train are approximately equal to the template.

6. The device of claim 3, wherein the means for determining whether one or more predetermined pacing pulse train requirements are satisfied determines one or more locations of evoked responses corresponding to morphologies determined not to be approximately equal to the template corresponding to the delivered pacing pulse train.

7. The device of claim 6, wherein the means for determining whether one or more predetermined pacing pulse train requirements are satisfied assigns one or more weighting factors in response to the determined one or more locations.

8. A method of validating a pacing pulse train associated with delivery of a high-energy pulse, comprising:

delivering the pacing pulse train to a chamber of a patient's heart;

generating evoked response data associated with the delivered pacing pulse train;

determining, in response to the generated evoked response data, whether one or more predetermined pacing pulse train requirements are satisfied; and identifying the pacing pulse train as being valid in response to the one or more requirements being satisfied; and responsive to the identification of the pacing train as valid, delivering the high-energy pulse to the chamber of the patient's heart at a predetermined delay following delivery of the pacing pulse train, wherein determining whether one or more predetermined pacing pulse train requirements are satisfied comprises:

comparing the generated evoked response data;

determining a temporal consistency of the compared evoked response data; and determining whether time intervals associated with a plurality of evoked responses corresponding to the pacing pulse train differ by more than a predetermined time period, wherein determining whether one or more predetermined pacing train requirements are satisfied further comprises determining one or more locations of temporally inconsistent evoked response data along the delivered pacing train, and wherein determining whether one or more predetermined pacing pulse train requirements are satisfied comprises assigning one or more weighting factors in response to the determined one or more locations.

9. A method of validating a pacing pulse train associated with delivery of a high-energy pulse, comprising:

delivering the pacing pulse train to a chamber of a patient's heart;

generating evoked response data associated with the delivered pacing pulse train;

determining, in response to the generated evoked response data, whether one or more predetermined pacing pulse train requirements are satisfied; and identifying the pacing pulse train as being valid in response to the one or more requirements being satisfied; and responsive to the identification of the pacing train as valid, delivering the high-energy pulse to the chamber of the patient's heart at a predetermined delay following delivery of the pacing pulse train, wherein determining whether one or more predetermined pacing pulse train requirements are satisfied comprises:

comparing the generated evoked response data;

determining a temporal consistency of the compared evoked response data; and determining whether time intervals associated with a plurality of evoked responses corresponding to the pacing pulse train differ by more than a predetermined time period, wherein the pacing pulse train includes a last pacing pulse and determining whether one or more predetermined pacing pulse train requirements are satisfied further comprises determining whether temporally inconsistent evoked response data corresponds to the last pacing pulse.

10. A method of validating a pacing pulse train associated with delivery of a high-energy pulse, comprising:

delivering the pacing pulse train to a chamber of a patient's heart;

generating evoked response data associated with the delivered pacing pulse train;

determining, in response to the generated evoked response data, whether one or more predetermined paving pulse train requirements are satisfied; and identifying the pacing pulse train as being valid in response to the one or more requirements being satisfied; and responsive to the identification of the pacing train as valid, delivering the high-energy pulse to the chamber of the patient's heart at a predetermined delay following delivery of the pacing pulse train, wherein determining whether one or more predetermined pacing pulse train requirements are satisfied comprises:

determining morphology of an evoked response on response to the evoked response data; and comparing the determined morphology to a predetermined evoked response morphology template.

11. The method of claim 10, wherein the requirements include one of evoked response morphology, temporal consistency of the evoked response, and cross correlation of sensing of the evoked response from multiple sensing locations.

12. The method of claim 10, wherein determining whether one or more predetermined pacing train requirements are satisfied further comprises determining whether a predetermined number of determined morphologies associated with the delivered pacing train are approximately equal to the template.

13. The method of claim 10, wherein determining whether one or more predetermined pacing train requirements are satisfied further comprises determining a proximity of evoked responses corresponding to morphologies determined not to be approximately equal to the template along the delivered pacing pulse train.

14. The method of claim 13, wherein determining whether one or more predetermined pacing pulse train requirements are satisfied comprises assigning one or more weighting factors in response to the determined one or more locations.

15. A medical device capable of generating pacing pulse and high-energy pulse, comprising:

means for delivering the pacing pulse to a chamber of a patient's heart;

means for determining whether a delivered pacing pulse successfully captured the chamber of the patient's heart; and means responsive to a determination that the delivered pacing pulse successfully captured the chamber of the patient's heart for delivering the high-energy pulse to the chamber of the patient's heart at a predetermined delay following delivery of the pacing pulse.

16. A medical device according to claim 15, wherein the pacing pulse delivery means comprises means for delivering a train of pacing pulses.

17. A medical device according to claim 16 wherein the determining means comprises means for determining whether a final pulse in the pacing pulse train successfully captured the chamber of the patient's heart.

18. A medical device according to claim 15 wherein the determining means comprises means for determining whether a required number of pacing pulses in the pacing pulse train successfully captured the chamber of the patient's heart.

19. A method of applying pacing pulses and high-energy pulses, comprising:

delivering the pacing pulses to a chamber of a patient's heart;

determining whether a delivered pacing pulse successfully captured the chamber of the patient's heart; and responsive to a determination that the delivered pacing pulse successfully capture the chamber of the patient's heart, delivering the high-energy pulse to the chamber of the patient's heart at a predetermined delay following delivery of the pacing pulse.

20. A method according to claim 19, wherein delivery the pacing pulses comprises delivering a train of pacing pulses.

21. A method according to claim 20 wherein determining whether a delivered pacing pulse successfully captured the chamber of the patient's heart means comprises determining whether a final pulse in the pacing pulse train successfully captured the chamber of the patient's heart.

22. A method according to claim 20 wherein determining whether a delivered pacing pulse successfully captured the chamber of the patient's heart comprises determining whether a required number of pacing pulse in the pacing pulse train successfully captured the chamber of the patient's heart.

* * * * *

UNITED STATES PATENT AND TRADEMARK OFFICE
CERTIFICATE OF CORRECTION

PATENT NO.       : 7,634,316 B2                                Page 1 of 1
APPLICATION NO.  : 11/117593
DATED            : December 15, 2009
INVENTOR(S)      : Swerdlow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 999 days.

Signed and Sealed this

Ninth Day of November, 2010

David J. Kappos
*Director of the United States Patent and Trademark Office*